United States Patent
Harvey (10) Patent No.: US 6,611,806 B1
(45) Date of Patent: Aug. 26, 2003

(54) LOT TRACKING SYSTEM FOR PHARMACEUTICALS

(75) Inventor: Joseph William Harvey, Fallbrook, CA (US)

(73) Assignee: FFF Enterprises, Inc., Temecula, CA (US)

( * ) Notice: Subject to any disclaimer, the term of this patent is extended or adjusted under 35 U.S.C. 154(b) by 0 days.

(21) Appl. No.: 09/291,421

(22) Filed: Apr. 13, 1999

(51) Int. Cl.[7] ............................................... G06F 17/60
(52) U.S. Cl. ................................................ 705/2; 705/7
(58) Field of Search .................... 705/2, 3, 7

(56) References Cited

U.S. PATENT DOCUMENTS

| | | | | |
|---|---|---|---|---|
| 5,301,105 A | * | 4/1994 | Cummings, Jr. ............ | 364/401 |
| 5,781,442 A | * | 7/1998 | Engleson et al. ...... | 364/478.02 |
| 6,021,392 A | * | 2/2000 | Lester et al. .................... | 705/2 |
| 6,163,781 A | * | 12/2000 | Wess, Jr. .................... | 707/103 |

FOREIGN PATENT DOCUMENTS

| WO | WO-98/50840 A2 | * | 11/1998 |
|---|---|---|---|
| WO | WO-98/50873 A1 | * | 11/1998 |

OTHER PUBLICATIONS

Joe Speed and E. Frank Antoine, Lot Number Recognition and Recording, The Canadian Journal of Hospital Pharmacy, vol. 2 Jul.–Aug., 1970, pp. 155–156.*
"Systems That Track Lot Numbers" (prior art). Attachment A Statement by Applicant.
"Hospital Database Systems" (prior art). Attachment B Statement by Applicant.

* cited by examiner

Primary Examiner—Richard Chilcot
Assistant Examiner—J Harle
(74) Attorney, Agent, or Firm—McDermott, Will & Emery (57) ABSTRACT

A computer system for tracking the lot numbers of pharmaceuticals that are administered to patients. The system includes a plurality of remote systems, each typically at a different hospital. Each remote system associates the lot numbers of pharmaceuticals that are administered to patients with information relating to the patients that receive the pharmaceuticals, and includes a remote communication system for sending the associations to a host system. The host system receives the associations from the remote systems, stores them, and consults the associations to identify recipients that need to be notified in connection with a lot number that needs to be tracked. The host system also includes a notification system for automatically issuing recall notices.

38 Claims, 6 Drawing Sheets

Data Tables

| System Name | Path | Database Name |
|---|---|---|

Patient Contact Information

| | | |
|---|---|---|
| Hospital ID | <map path to> | <database name> |
| Patient ID | <map path to> | <database name> |
| Patient Name | <map path to> | <database name> |
| Patient Address | <map path to> | <database name> |
| Patient Phone | <map path to> | <database name> |
| Patient E-mail | <map path to> | <database name> |
| Patient Fax | <map path to> | <database name> |
| Patient Social Security | <map path to> | <database name> |

Physician Contact Information

| | | |
|---|---|---|
| Hospital ID | <map path to> | <database name> |
| Physician ID | <map path to> | <database name> |
| Physician Name | <map path to> | <database name> |
| Physician Address | <map path to> | <database name> |
| Physician Phone | <map path to> | <database name> |
| Physician Fax | <map path to> | <database name> |
| Physician e-mail | <map path to> | <database name> |

Pharmaceutical Information

| | | |
|---|---|---|
| Hospital ID | <map path to> | <database name> |
| Pharmaceutical ID | <map path to> | <database name> |
| Pharmaceutical NDC No | <map path to> | <database name> |
| Pharmaceutical Code | <map path to> | <database name> |
| Pharmaceutical Descriptor | <map path to> | <database name> |

Prescription Information

| | | |
|---|---|---|
| Hospital ID | <map path to> | <database name> |
| Transaction ID | <map path to> | <database name> |
| Pharmaceutical ID | <map path to> | <database name> |
| Prescription number | <map path to> | <database name> |
| Quantity ordered | <map path to> | <database name> |
| Physician ID | <map path to> | <database name> |
| Patient ID | <map path to> | <database name> |
| Order administered | <map path to> | <database name> |
| ICD-9 code | <map path to> | <database name> |
| Adverse reaction | <map path to> | <database name> |

Lot Assignments

| | | |
|---|---|---|
| Hospital ID | <map path to> | <database name> |
| Assignment ID | <map path to> | <database name> |
| Prescription number | <map path to> | <database name> |
| Lot number | <map path to> | <database name> |

LOT TRACKING SYSTEM FOR PHARMACEUTICALS

BACKGROUND OF THE INVENTION

1. Field of the Invention

This invention relates to tracking the pharmaceuticals administered to patients.

2. Description of Related Art

There is great value in being able to quickly and efficiently track the patients to whom pharmaceuticals, such as blood derivatives, have been administered.

One example is product recall. Occasionally, a pharmaceutical will be recalled by its manufacturer or by the FDA. This occurs, for example, when a pharmaceutical is discovered to have been tainted by a pathogen of some type, by deficiencies in the manufacturing process, or to have suffered from a potency problem. Some years ago, for example, it was discovered that blood containing Hepatitis C was administered to approximately one million patients.

The ability to track pharmaceuticals to patients is also of great importance to research. Fast and efficient tracking can facilitate the evaluation of drug effectiveness. It can also facilitate an analysis of conditions for which a particular drug is being administered, information of vital importance to the manufacturers of those drugs and to others.

Our present system of medical care, however, does not provide a very effective method of tracking pharmaceuticals, including blood derivatives. When it is desired to track certain lot numbers of a pharmaceutical to the patients to whom they have been administered, there often are no records that can be consulted. Even when there are, the tracking is neither efficient, nor comprehensive.

SUMMARY OF THE INVENTION

One object of the present invention is to provide a lot tracking system for pharmaceuticals, including blood derivatives.

Another object of the present invention is to provide a lot tracking system for pharmaceuticals that will enable specified lot numbers of a pharmaceutical to quickly and efficiently be tracked to the patients to whom those lot numbers were administered.

Another object of the present invention is to provide a lot tracking system for pharmaceuticals that is able to complement existing hospital computer systems quickly and with a minimum of effort.

Another object of the present invention is to provide a lot tracking system for pharmaceuticals that is compatible with a wide variety of existing hospital database systems.

A still further object of the present invention is to provide a lot tracking system for pharmaceuticals that automatically makes use of existing databases of information, thus eliminating the need for the timely, costly and potentially error-prone duplication of information.

A still further object of the present invention is to provide a lot tracking system for pharmaceuticals that provides redundant data storage at both a secure and a remote location.

A still further object of the present invention is to provide a lot tracking system for pharmaceuticals that enables a central location to track pharmaceuticals that are administered at several hospitals.

A still further object of the present invention is to provide a lot tracking system for pharmaceuticals that protects the confidentiality of patient information.

A still further object of the present invention is to provide a lot tracking system for pharmaceuticals that automates the issuance of recall notifications.

A still further object of the present invention is to provide a lot tracking system for pharmaceuticals that tracks the status of recall notifications.

A still further object of the present invention is to provide a lot tracking system for pharmaceuticals that is easy to utilize and requires few steps to be performed to obtain the benefits of the invention, beyond those already being performed in systems that do not utilize the invention.

A still further object of the present invention is to provide a lot tracking system for pharmaceuticals that will readily enable the tracking of patient treatment outcomes, as well as a broad variety of other information useful to patient safety and medical research.

These as well as still further features, objects and benefits of the present invention are facilitated by an apparatus and process that utilizes a plurality of remote systems, typically installed at hospitals, a host system, and a communication network connecting the two.

In one embodiment, one remote system includes a plurality of remote stations, each for associating the lot numbers of pharmaceuticals administered to patients with information relating to the patients that receive the pharmaceuticals. A remote communication system is also provided in each system for sending the associations to a host system.

The host system contains a host communication system for receiving the communications from each of the remote systems. The host system further includes a storage area for storing the association's received from the remote communication systems.

When it is desired to track a particular lot number that is subject to an action, that number is entered into a station at the host system. That number is then looked up in a host look-up system to obtain the associations that are related to that lot number. Appropriate notices are then issued by a host notification system to recipients, based on the associations that are looked up by the host look-up system.

The communications between the remote systems and the host can be immediate, occasional or periodic. When occasional or periodic, the remote systems additionally include a storage area for storing the associations between lot numbers and the patient-related information.

In a preferred embodiment, much of the patient-related information is extracted from existing databases in each remote system. A map is advantageously used to associate the fields of information needed by the lot tracking system of the present invention with the fields of information that already exist in these databases.

In a still further embodiment of the present invention, the entry of a prescription for a pharmaceutical that is to be traced is automatically detected and automatically spawns subsequent date gathering and tracking functions.

In a still further embodiment of the present invention, the host notification system automatically issues notices of recalls and other tracking information to the recipients that have been indicated as being associated with the particular lot numbers of the pharmaceuticals that are the subject of the notifications. The host notification system further keeps track of the success of the notifications and, in one embodiment, produces reports of the notification efforts that have been made.

In a still further embodiment of the present invention, the lot tracking system includes validation features for validating the accuracy of lot numbers that are entered and for validating and updating the stored contact information.

In a still further embodiment of the present invention, a transaction tracking system is advantageously employed to make a record of each of the operational steps through which the system has gone.

Although having been thus-far described in the context of a tracking system for pharmaceuticals, a still further embodiment of the present invention is more broadly applicable to tracking all types of products, not merely pharmaceuticals.

The invention is directed to the apparatus that implements the invention, the storage media that stores the software programs used in some embodiments of the invention, and the process of the invention.

These as well as still further objects, features and benefits of the present invention will now become clear upon a review of the following Detailed Description of the Preferred Embodiments, along with the attached drawings.

BRIEF DESCRIPTION OF THE DRAWINGS

FIG. 3 describes various data tables that are used in one embodiment of the present invention, including tables of patient-related information.

DESCRIPTION OF THE PREFERRED EMBODIMENTS

Figure 1:
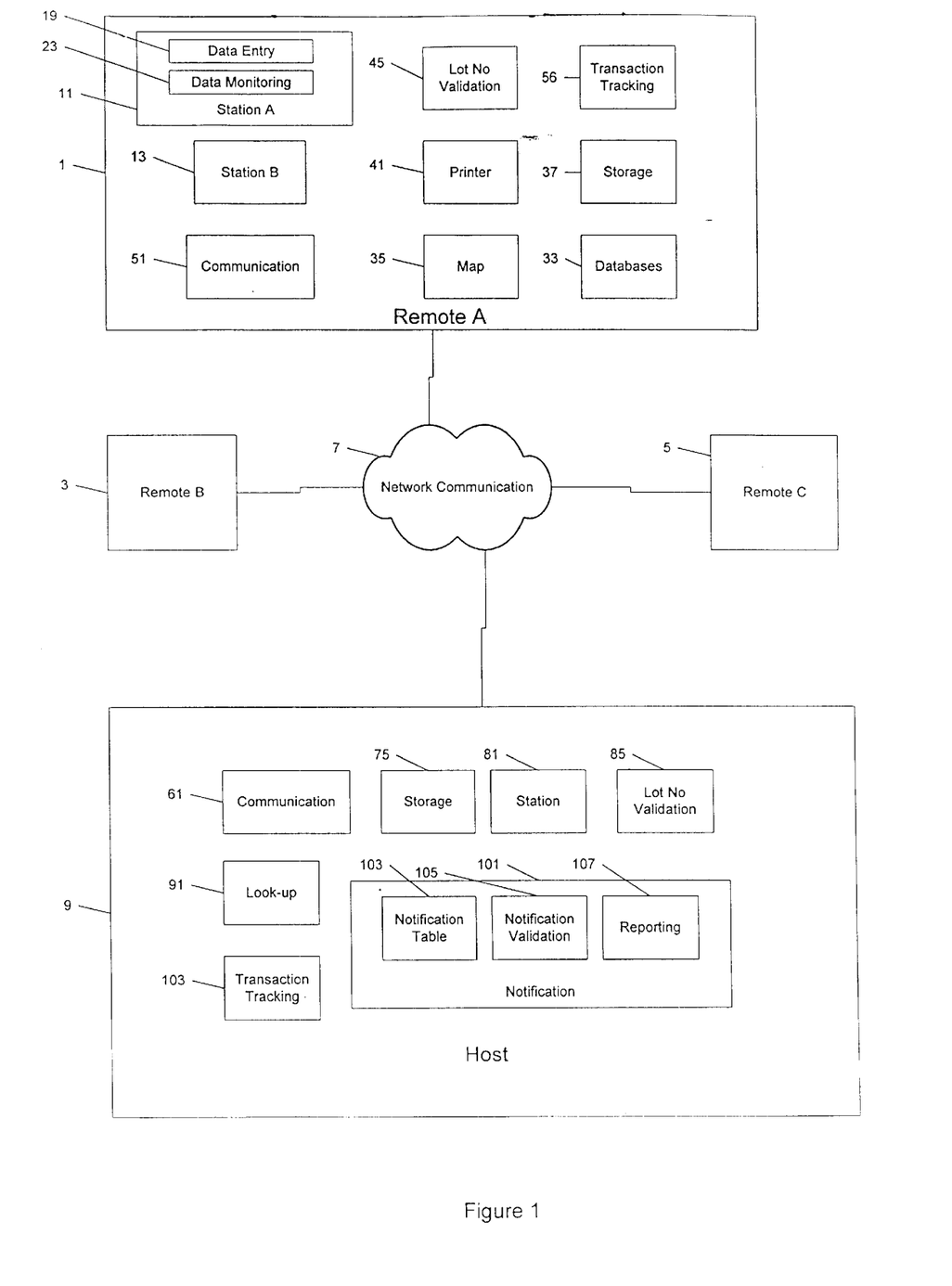
FIG. 1 is a block diagram of a lot tracking system for pharmaceuticals made in accordance with one embodiment of the present invention.

FIG. 1 is a block diagram of a lot tracking system for pharmaceuticals made in accordance with one embodiment of the present invention.

As shown in FIG. 1, the lot tracking system includes a plurality of remote systems, such as remote systems 1, 3 and 5. These remote systems are connected through a network communication system 7 to a host 9.

In one embodiment of the invention, one or more of the remote systems are installed in a hospital, pharmacy, physician's office, ambulance, or other medical facility. Although not required, the remote systems are also often integrated with other computer systems at the remote site. Although only three remote systems are illustrated in FIG. 1, it is of course to be understood that the invention contemplates any number of remote systems, generally greater than one.

The host system 9 is generally at a location that is remote from the remote systems. As will soon be seen, this can facilitate a degree of data redundancy that protects the data in the event of a catastrophic loss. Although generally not as preferred, the invention also contemplates that the host system 9 could be physically located in the same vicinity as any one of the remote systems.

The network communication systems 7 can be of any type. As is well known in the art, such systems include the Internet, including web-based systems and virtual private networks, private dial-up connections, wireless connections, and all other types of data communication systems.

Figure 2:
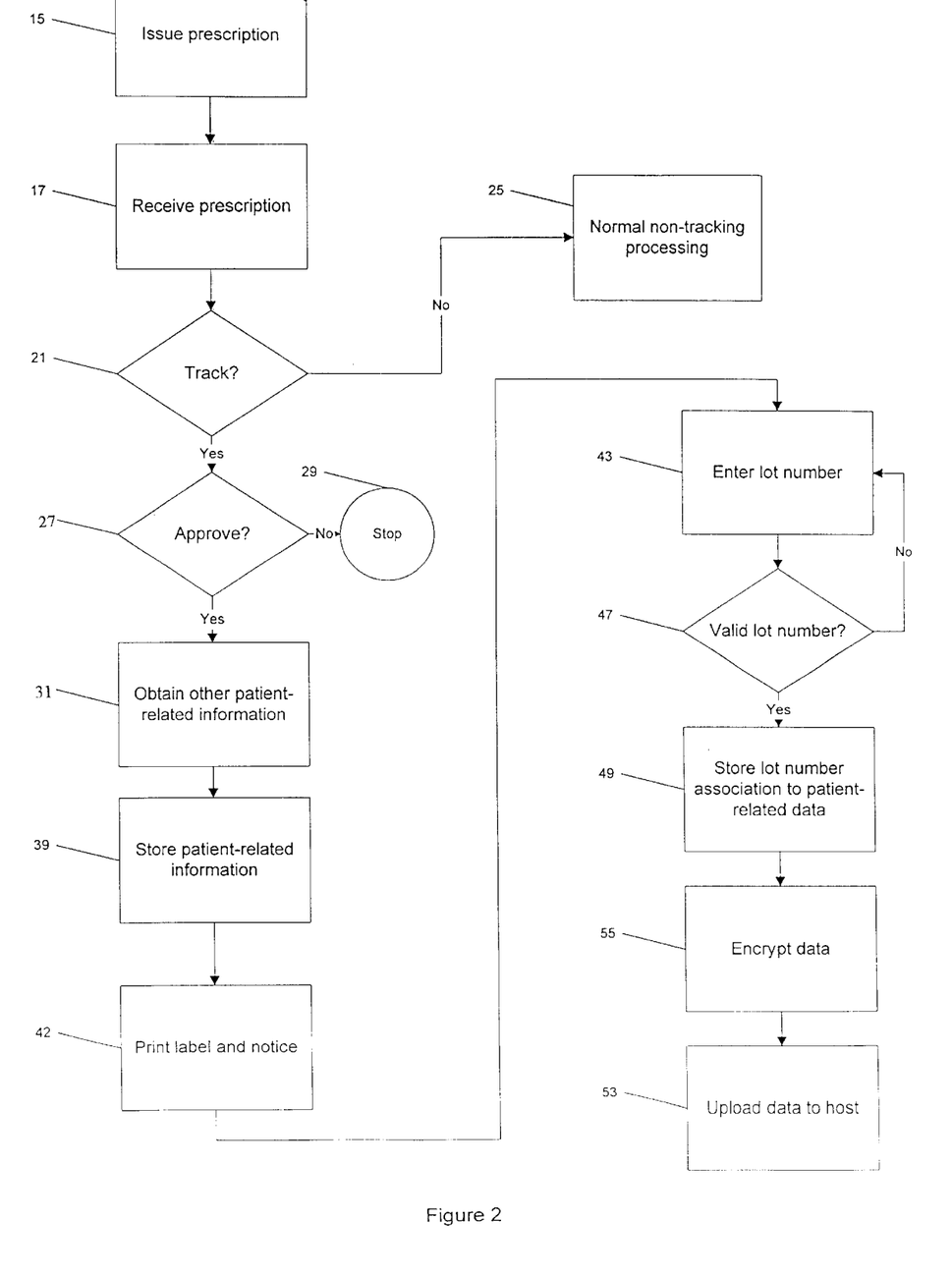
FIG. 2 is a flow diagram of the process implemented by one of the remote systems shown in FIG. 1 in accordance with one embodiment of the present invention.

FIG. 2 is a flow diagram of the process implemented by one of the remote systems shown in FIG. 1, such as the remote system 1, in accordance with one embodiment of the present invention. The composition of the remote system 1 as shown in FIG. 1 will now be discussed in conjunction with the operation of this remote system as illustrated in FIG. 2.

Typically, a physician issues a prescription for a patient to receive a particular pharmaceutical, such as a blood derivative, as illustrated by an Issue Prescription block 15 in FIG. 2. Prescriptions may be recorded on paper or, in a more modern facility, entered into a computer.

A key feature of the present invention is to record an association between each prescription issued by the physician which is to be tracked and the lot number or numbers of the pharmaceuticals that are actually administered to the patient in fulfillment of the prescription. Although referring to the information that identifies a particular pharmaceutical as a lot number, it is to be understood that the phrase "lot number" is intended to connote any type of information that is used to identify the pharmaceutical, whether it is called a "lot number" or not. This includes information that identifies a particular batch or set of products that is administered to a patient, or any other type of organizational arrangement.

The initial associations are typically made through the use of one or more remote stations, such as the remote stations 11 and 13 shown in FIG. 1.

The next step is for the prescription to be received by a remote station, such as the remote station 11 in FIG. 1, as illustrated by a Received Prescription block 17 in FIG. 2.

The invention embraces a broad variety of mechanisms for accomplishing this result.

In one embodiment, the remote station 11 is used by the pharmacist. If the prescription is received by the pharmacist on a piece of paper, the pharmacist enters the details of the prescription in the station 11 under the control of a data entry program 19 that is controlling the operation of the station 11. The fields of information that are entered can vary widely. Typically, they will include information relating to the patient, the patient's physician, the prescribed pharmaceutical, the quantity ordered and the prescription number.

In an alternate embodiment of the invention, the prescription information is entered at another station (not shown in the figures) and is delivered over a computer network to the pharmacist at the station 11 for further processing.

In either case, the next step in accordance with one embodiment of the present invention is to determine whether the prescription is directed to one of the pharmaceuticals that should be tracked by the present invention, as reflected by a Track? block 21 in FIG. 2.

In some embodiments of the invention, tracking of all types of pharmaceuticals will be desired. In these embodiments, a decision about tracking does not need to be made. In other embodiments, however, there will not be a desire to track all types of pharmaceuticals, but only some of them. In these embodiments, the tracking decision reflected by the Tract? block 21 in FIG. 2 will need to be made.

For those embodiments in which a tracking decision is to be made, the invention contemplates all methods and techniques for making this decision. One technique is to compare the prescribed pharmaceutical with a list of pharmaceuticals that are to be tracked. If the prescribed pharmaceutical matches an entry in the list, this of course means that the prescribed pharmaceutical should be tracked. If the prescribed pharmaceutical is not in the list, this of course means that the prescribed pharmaceutical need not be tracked.

Another benefit of the present invention is that it can be installed at the remote site, such as a hospital, with a minimum of effort. It also can be operated at the remote site with minimal changes in their operational procedures.

In one embodiment of the present invention, these benefits are facilitated by adding a data monitoring program 23 to the remote station 11. In this embodiment, the data entry program 19 is the data entry program that the remote station 11 was using prior to upgrading to implement the present invention.

In order to implement this embodiment of the present invention, the data monitoring program 23 is simply added and runs in the background. While running in the background, the data monitoring program 23 monitors the data that is entered and managed by the data entry program 19 for the entry of a prescription that needs to be tracked, e.g., a prescription that has been listed in a table of prescriptions to be tracked. In other words, the data monitoring program 23 operates in the background and monitors the prescriptions that are being processed by the station 11 in search of a prescription that is to be tracked.

As a result, the monitoring function is transparent to the user. In one embodiment, the running of the background data monitoring program 23 is inconspicuously indicated to the user of the station 11 by a small icon at the bottom of the desktop of the station 11.

The invention embraces all techniques for performing this background-monitoring function, including the many that are well-established and understood, including screen scraping, direct database calls, and the monitoring of API calls.

If the prescribed pharmaceutical is not listed in the table of pharmaceuticals to be tracked, the normal processing of such pharmaceuticals on remote entry station 11 would then proceed, as reflected by a Normal Non-Tracking Processing block 25 in FIG. 2. If the prescribed pharmaceutical is on the list of pharmaceuticals to be tracked, on the other hand, the next step of this embodiment of the invention is to proceed to the Approve box 27 in FIG. 2.

The Approve box 27 is directed to the existing process that the pharmacist follows to approve the prescription before the prescribed pharmaceutical is dispensed. As is well known, approval of a prescription by a pharmacist is a well-respected and widely implemented patient safeguard in the prescription process.

In one embodiment of the present invention, the pharmacist signifies his approval or disapproval by making appropriate entries under the control of the data entry program 19 in the remote station 11, just like he did prior to upgrading to implement the present invention.

In one embodiment of the present invention, status of this approval is also monitored by the data monitoring program 23. If approval is not given, tracking of the prescribed pharmaceutical is halted, as reflected in the Stop block 29 in FIG. 2. If approval is given, on the other hand, the invention proceeds to an Obtain Other Patient Related Information block 31, as also reflected in FIG. 2.

Although the decision to track has thus-far been discussed and illustrated as proceeding the decision to approve, it is to be understood that the invention contemplates that the approval step 27 might precede the tracking step 21. Similarly, although disapproval has thus-far been described as causing a cessation in the tracking efforts, it is also to be understood that the invention contemplates tracking of the disapproval, as well.

The invention embraces all techniques for performing the Obtain Other Patient-Related Information block 31 just discussed. The invention also embraces systems that obtain no further patient-related information, beyond the patient-related information that has already been processed by the station 11.

In one embodiment of the present invention, the other patient-related information is obtained automatically from databases 33 in the remote system 1. This process is advantageously effectuated through the use of a map 35 in the remote system 1.

In this embodiment, the map 35 maps those fields of information that the lot tracking system of the present invention utilizes, called system fields, to the actual fields of information that are stored in the databases 33, called database fields.

For example, the prescription that the pharmacist handles in the station 11 may refer as to the patient by only the number that has been assigned to the patient by the remote site 1. In order to obtain the name of the patient in this example, the system of the present invention utilizes the map 33 to map the system fields for the patient's number and name to the corresponding database fields in the databases 33 that contain this information.

FIG. 3 describes various data tables that are used in one embodiment of the present invention, including a table of "Lot Assignments," and tables of patient-related information, such as "Patient Contact Information," "Physician Contact Information," "Pharmaceutical Information" and "Prescription Information."

The fields in the left-hand column labeled "System Name" refer to the names these fields have been given by the system of the present invention. The fields in the right-hand column labeled "Database Name" refer to the names these fields are given in the databases 33. The middle column labeled "Path" sets forth the mapping information that points to each database name, i.e., the information that is necessary to associate each system field with its corresponding database field.

Through the use of this mapping information, additional fields of patient-related information that are to be tracked are extracted from the databases 33 using well known database mapping techniques. All such technologies are embraced by the invention.

Through the use of this technology, the invention can easily and readily be adapted to a broad variety of database systems.

As reflected by FIG. 3, these tables embrace a broad variety of information. The first table in FIG. 3 is directed to "Patient Contact Information." As reflected by the system names of this information, this is information that will readily facilitate communication with a patient who receives a particular pharmaceutical that is being tracked.

Another class of patient-related information is the "Physician Contact Information" table, also shown in FIG. 3. As reflected by the system names of the fields in this table, this is information that will enable communication with the physician that is treating the patient. Such information is also of obvious importance in the tracking process.

The next table in FIG. 3 is "Pharmaceutical Information." As reflected by the system names of these fields, this is information about the various pharmaceuticals that may be prescribed. The information in this table can advantageously be consulted to determine whether the prescription is directed to a pharmaceutical that is to be tracked, as discussed above in connection with the Track? block 21 in FIG. 2.

The next table in FIG. 3 is for "Prescription Information." As reflected by the system names of these fields, this is information about each particular prescription, such as the information that was discussed above in connection with the prescription that was processed by the station 11. As reflected in this table, this particular embodiment of the present invention also tracks whether the prescription has actually been administered to the patient under the "Order Administered" field, the patient's reaction to the prescription under the "ICD-9 code" field, and any adverse reactions under the "Adverse Reaction" field. Of course, these are data entries that are usually made later, after the processing of the prescription, as will be discussed below.

The last table listed in FIG. 3 is "Lot Assignments." As will be discussed below, this table records the associations that will soon be made between prescriptions and the lot numbers of the pharmaceuticals that are administered to the patients as a result.

Of course, it should be understood that the invention contemplates all variations in the types of tables and data fields that are created and stored. The invention also embraces the use of additional tables, as well as a lesser number of tables. Although each field under the "System Name" column is indicated as having an associated "Database Name" mapped to it, it should also be understood that, in practice, some or even all of these system fields may not have any associated counterpart in the databases 33. In these instances, the information will need to be entered manually (or from some other source) or will not be included.

The Obtain Other Patient-Related Information block 31 thus describes the process of assembling all of the predetermined patient-related information that is to be tracked after entry and approval of a prescription that is to be tracked, such as the fields of information discussed above.

At this point in the process, of course, the lot number of the pharmaceutical that is actually administered to the patient is not yet available. However, everything but the lot number is available and is gathered at this point.

Of course, the invention is not limited to systems which gather this other information at this point in time. Indeed and as indicated above, the invention embraces systems in which no further information is gathered.

In the embodiment of the invention that does gather this other information at this point in time, it is often advantageous to store that gathered information locally at the remote station 1 in a remote storage area 37, as shown in FIG. 1, and as illustrated by the Store Patient-Related Information block 39 in FIG. 2.

As will later be seen, this is only an interim storage step. As will also later be seen, it provides the advantage of data redundancy and eliminates the need for an immediate communication to the host 9. As indicated above, however, it is not an essential step, nor is its performance at this moment essential.

The invention embraces all of the different permutations of structures and content for the patient-related information that is stored in the storage area 37. In one embodiment, for example, many if not all of the fields of actual information are duplicated and stored in appropriate tables in the storage area 37. In other embodiments, only pointers to the actual fields of information are stored. In still further embodiments, none or only portions of this information is duplicated and stored in the storage area 37.

After the Track block 21, Approve? block 27, Obtain Other Patient-Related Information block 31 and Store Patient-Related Information block 39 are performed, as shown in FIG. 2, the label for the prescription is printed on a printer 41 in FIG. 1, along with a notice to the technician that will actually dispense the prescription, advising him that the lot-numbers of this particular prescription must be tracked. This sequence is indicated by a Print Label and Notice block 42 in FIG. 2. This is similar to the manner in which the remote system 1 operated prior to being upgraded to incorporate the invention, except that the printer 41 now additionally prints out a notice to the technician to record the lot numbers.

In one embodiment of the present invention, the instruction to the technician is included with the label; in another embodiment, it is separately printed. In a still further embodiment (not shown), the instruction to record the lot-numbers can be provided to the technician through other means, such as a computer display, such as the display associated with station 13.

Preferably, the printer 41 is in the vicinity of where the technician works, who typically is someone other than the pharmacist. Upon receiving the printout of the label and notice, the technician typically fills the prescription. With the implementation of the present invention, the technician need only walk over to the computer station 13 in his area and enter the lot-number (or numbers) of the pharmaceuticals that he selected to fulfill that prescription, as reflected by an "Enter Lot Number" block 43 in FIG. 2.

Software is run in his station 13 that receives the prescription information from the pharmacist station, such as station 11. The technician simply associates the lot number (or lot numbers) of the pharmaceuticals that he has supplied by entering that lot number (or those lot numbers) in the station 13 in the area that corresponds to the prescription that he has filled.

The process of the present invention has thus-far been described as involving two individuals—the pharmacist and a technician—entering data into two separate station—stations 11 and 13. However, the invention is equally applicable to having this information entered by more than two individuals and/or using more than two stations. Conversely, the pharmacist and technician could use the same station, or all of the process that has thus-far been described could be done by a single person, such as a nurse In a still further embodiment, the functions provided by each station and the number of stations that are needed to complete the association of lot numbers to pharmaceuticals may automatically change, depending upon the identity and associated qualifications of the user of the station(s).

In a still further embodiment, the functions of the stations 11 and/or 13 could be performed by an automated drug dispensing machine. Such an automated dispensing machine is squarely within the scope of what is referred to as a "station" in this application.

Although a single lot number will commonly be entered for a single prescription, the station 13 is also usually configured to allow multiple lot numbers to be entered for a single prescription. Such a situation can arise, for example, when the quantity of the prescription requires a contribution from different lots. Although the discussion which now follows will refer to a single lot number for each prescription, it is therefore to be understood that it also embraces the association of multiple lot numbers with each prescription.

The invention contemplates a broad variety of mechanisms for accomplishing the entry of the lot numbers. In one embodiment, they are entered manually by the operator. In another, the pharmaceuticals contain a bar code that is optically read.

After the lot number is entered, a validation step may next be performed by a lot number validation system 45 in FIG. 1, as reflected by a Valid Lot Number block 47 in FIG. 2. Validation of the entered lot number, of course, is not an essential step. But it can be advantageous in many situations.

The invention embraces all techniques for validating lot numbers. In one embodiment, the lot number validation system 45 compares each lot number that has been entered with the lot numbers that had previously been entered when the pharmaceuticals were purchased which, for example, are stored in areas of the databases 33. For maximum protection, it is important that the station 13 not allow the lot number that is entered to be selected from a pick-list, but rather forces it to be entered manually, digit-by-digit.

The associations between the entered lot number and the patient-related information is then stored in storage 37, as reflected by a Store Lot Number Association to Patient-Related Data block 49 in FIG. 2. As will soon be seen, this provides a redundant level of storage and alleviates the need for the remote system 1 to immediately communicate with the host 9 at this point in time.

As with the storage of the patient-related information discussed above, the invention embraces all methods and approaches for storing the associations in the storage area 37. For example, the storage might only be of pointers that point to actual locations of the actual lot numbers and/or the patient-related information. Alternatively, duplicates of this information may be extracted from the databases 33 and stored in a relational format in the storage area 37.

After creation and storage of the association between the lot number and the prescription, further useful information can be added, such as an indication whether the pharmaceutical has actually been administered to the patient in the "Order Administered" field in the "Prescription Information" table in FIG. 3; the condition of the patient under the "ICD-9 Code" field in the same table; and any adverse reactions exhibited by the patient under the "Adverse Reaction" field in the same table. This information could advantageously be stored in the databases 33 with or without pointers to it being stored in the storage area 37. Alternatively or in addition, this information could be directly and exclusively stored in the storage area 37.

Lot numbers and associated patient-related information are delivered to the host 9 over the network communication 7 by a communication system 51, as reflected by an Upload Data to Host Block 53 in FIG. 2. To protect the confidentiality of the information and for other security purposes, at least portions of this information are first encrypted, as reflected by the Encrypt Data Block 55 in FIG. 2.

Communication system 51, of course, needs to be compatible with the network communication system 7. Depending upon the particular type of network communication system 7 that is being used, the communication system 51 may include communication software and communication hardware, such as a modem or a direct connection to the Internet.

In a still further embodiment of the present invention, a transaction tracking system 56 is included in the remote system 1. The transaction tracking system 56 keeps a record of some or all of the operations that take place at the remote system 1. Such a record is often quite useful in connection with a wide variety of accounting activities, as well as providing a mechanism for reconstructing damaged data.

In those embodiments of the invention that do not utilize the separate storage area 37, it will be necessary to deliver the information associating lot numbers with patient-related information to the host 9 as soon as the information is generated. To avoid the requirement for constant communications with the host, however, the storage area 37 is included. The inclusion of the storage area 37 is only necessary when the association information is only uploaded to the host occasionally or on a periodic basis.

For those configurations in which the information is only uploaded on an occasional or periodic basis, the system may be configured for the remote 1 to initiate the communication with the host 9, or for the host 9 to initiate the communication with the remote 1. Indeed, the system can be configured for the host 9 to poll certain remote stations, while other remote stations are configured to automatically upload their information to the host 9 on a periodic basis.

The host system 9 shown in FIG. 1 provides two primary functions: the downloading of association information from the remote stations and the issuance of tracking notifications.

Figure 4:
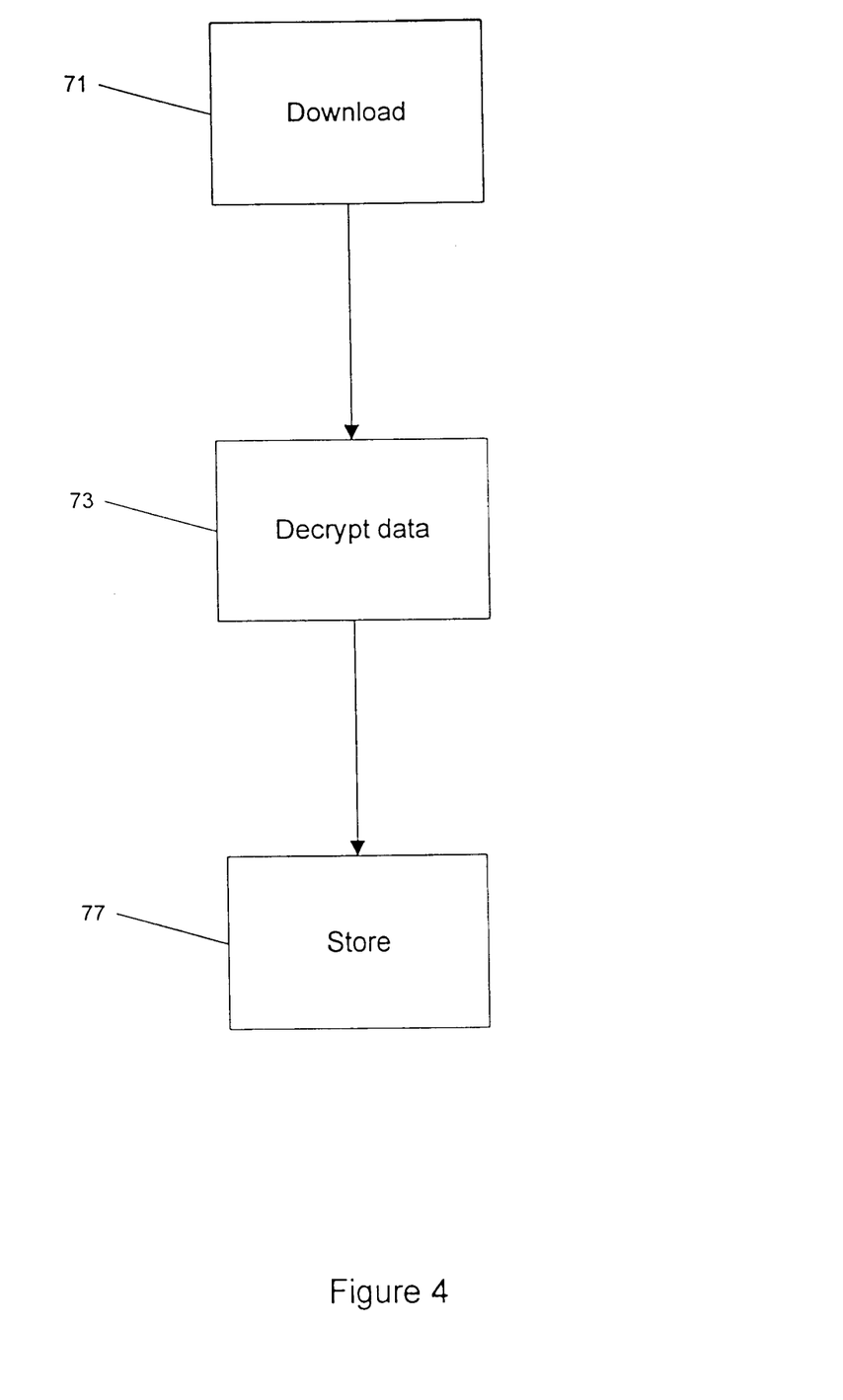
FIG. 4 is a flow diagram of the downloading and storage process implemented by the host system shown in FIG. 1 in accordance with one embodiment of the present invention.

FIG. 4 is a flow diagram of the downloading function implemented by the host system 9 shown in FIG. 1 in accordance with one embodiment of the present invention. The network communication system 7 is connected to the host communication system 61. This communication system is typically a mirror image of the remote communication system 51. Of course, it might also be quite different in composition. Like the remote communication system 51, however, it must, of course, be compatible with the network communication system 7. As shown by a Download Block 71 in FIG. 4, the communication system 61 downloads the association information from the network communication system 7. When a portion of the information has been encrypted, it may first be decrypted, as reflected by a Decrypt Data block 73 in FIG. 4. The resulting information is then stored in a storage area 75, as reflected by a Store block 77 in FIG. 4.

For greater security, however, particularly in connection with the name of the patient, the remote system 1 may not give the host the key it needs to perform the decryption operation. In this instance, the decryption operation denoted by the Decrypt Data block 73 is not performed, and the information is instead stored in the storage area 75 in its encrypted format.

Figure 5:
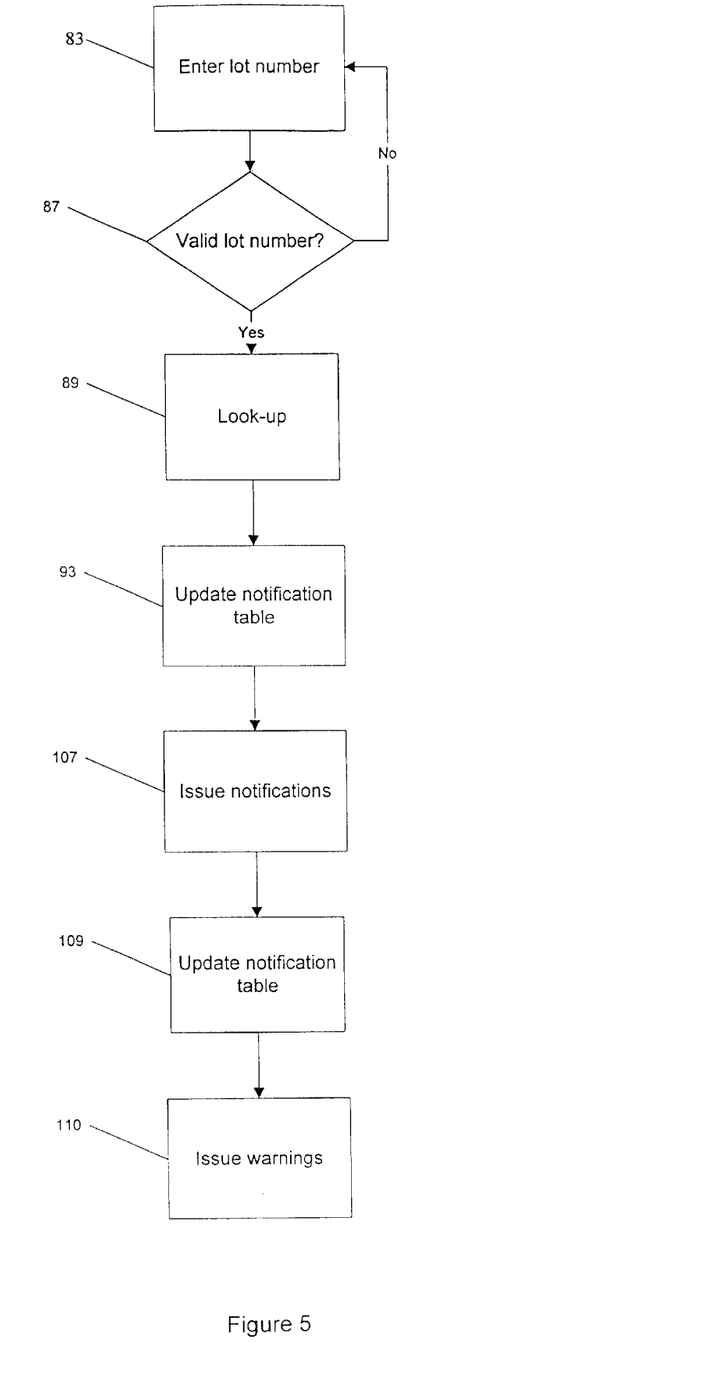
FIG. 5 is a flow diagram of the notification process implemented by the host system shown in FIG. 1 in accordance with one embodiment of the present invention.

FIG. 5 is a flow diagram of the notification process implemented by the host system shown in FIG. 1 in accordance with one embodiment of the present invention.

As discussed above, it frequently is desirable to issue certain types of notifications in connection with particular lot numbers of a pharmaceutical, such as a recall notification. In such an instance, the lot numbers of the pharmaceuticals that are the subject of the notification are entered into a station 81, as reflected by the Enter Lot Number block 83 in FIG. 5. In one embodiment of the invention, the validity of this entry is verified by a lot number validation system 85, as reflected by a Valid Lot Number? block 87 in FIG. 5. The same techniques as discussed above in connection with the lot number validation system 45 in the remote station 1 may advantageously be used here.

After validation (or after entry of the lot number without validation), the patient-related information that is associated with the lot number is looked up by a look-up system 91 from the storage area 75, in accordance with well known techniques, as illustrated by a Look-up block 89 in FIG. 5.

The host system 9 then issues notices of the pharmaceuticals that need to be tracked to the recipients based on the associations looked up by the look-up system 91 in the storage area 75. The recipients, of course, are the patients, doctors, hospitals, and other entities and locations that have been associated with the lot number.

The invention embraces a broad variety of notices. In one embodiment, some or all of the notices are informational memorandum, containing details about the notification. In another embodiment, some or all of the notices are a report of all of the associations issued for the operator to handle in either electronic or hard copy form. In a still further embodiment, some or all of the notices are e-mails, faxes, pager calls, and even voice phone calls that are automatically issued by the system. In a still further embodiment, some or all of the notices are delivered over the communication network 7 to the appropriate remote systems, including in some embodiments remote systems from which the associations were not received, and, thereafter, to the appropriate individuals or departments either within or without the structure of the remote systems. In still further embodiments, the notices are a combination of one or more of these, as well as other formats and mechanisms.

The invention also contemplates a broad variety of techniques for implementing and tracking the notification process. In one embodiment, a notification system 101 is utilized that includes a notification table 103, a notification validation system 105 and a reporting system 107.

In this embodiment, the contact information that is associated with each entered lot number that is looked up is entered into the notification table 103, as reflected by an Update Notification Table 93 block in FIG. 5. In one embodiment, the table 103 is configured to store a list of contacts to be notified, the notification to be provided to each contact, and the status of each notification.

The notification system 101 then proceeds to issue each of the notifications that are required, as reflected by an Issued Notifications block 107 in FIG. 5. As discussed above, these include the automated delivery of e-mail, a fax, a pager call, a voice telephone call, and the delivery of messages back into the communication network 7 to one or more of the remote stations. It also includes the simple generation of a notification report, as also explained above.

Some of the notification techniques, particularly the automated ones, might fail for various reasons. After each notification effort, the notification table 103 is updated by the notification system 101, as reflected by an Update Notification Table block 109. if a notification is unsuccessful after one or a pre-determined number of attempts, a report is issued by the reporting system to provide a warning about the unsuccessful notification, as reflected by an Issue Warnings block 110 in FIG. 5. Of course, the report can also advantageously list successful notifications, if desired.

As the contact information stored in the storage area 75 ages, its accuracy will be compromised by changes in addresses or contact information of the individuals. To help maintain this information current, the notification system 101 may advantageously further include the notification validation system 105 that updates the patient-related information stored in the storage area 75 with more current information.

The invention contemplates a broad variety of techniques for obtaining this updated information. For example, it may be sent by one or more of the remote stations in connection with updates. Alternatively, or in addition, the notification validation system 105 may periodically access outside databases of information, such as telephone directories and appropriate Internet websites.

As with the remote system 1, the host system 9 may additionally include a transaction tracking system 103. This transaction tracking system has the same function as the transaction tracking system 56 in the remote system 1. It records some or all of the operations of the host system 9 to facilitate later accountings and/or the reconstruction of damaged data.

A still further and equally significant feature of the present invention is that it is easy to install in existing systems and even easier to operate.

One key component of this configuration is the data tables shown in FIG. 3 and the mapping function which these tables provide. With such a configuration, all of the existing data becomes immediately available on an automated and transparent basis to the new system. In order to install the new system (i.e., a system implementing the present invention) at a remote site, the installer merely needs to enter the paths and database name information in the data tables and to then load the additional software components needed to implement the invention, such as the data monitoring program 23. Most existing remote locations will already have all or almost all of the necessary hardware already installed, such as the remote stations 11 and 13, the printer 41, the storage area 37, as well as most of the needed software, such as the databases 33 and the associated software used to manage them, and the data monitoring program 23.

But because the data monitoring software 23 runs in the background, the pharmacist who operates the station 11 will not need to learn or do virtually anything new. Indeed, the only routine operational function that will usually need to be added is the entry of lot numbers in the station 13.

Figure 6:
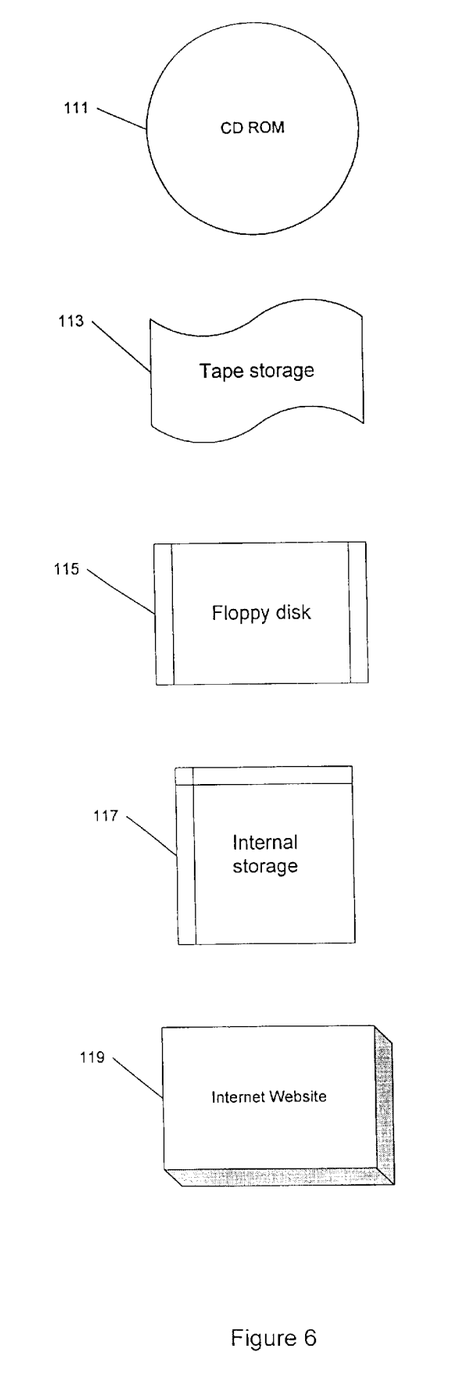
FIG. 6 illustrates various media on which software implementing one embodiment of the present invention is stored.

As indicated, the invention contemplates that many of its functions will be implemented by software programs. For installation and transfer purposes, these programs may be advantageously stored on computer-storage media, such as a CD ROM 111, tape storage 113, floppy disk 115 internal storage device 117, or an Internet website 119 shown in FIG. 6, or on a plurality or mixture of them.

The invention is also by no means limited to the particular embodiments that have been discussed above, or to even the variations that have been discussed in connection with them. For example, the invention also embraces systems which do not have many of the components that have been discussed above and/or which have additional components. Examples of such additional components include software and hardware to archive data that is stored at the remote and/or host locations and/or to automatically delete data that has been downloaded to the host and/or data that is no longer of interest. With a slight and obvious modification, moreover, the present invention can also be advantageously used to warn a technician when he is about to fill a prescription with a lot number that has previously been recalled.

The present invention is not even limited to having the components of either the remote or the host systems being at the same or at separate locations. The invention also contemplates that the functions of the invention will be implemented by hardware, software, firmware or by a combination of these, all in accordance with techniques that are well known.

In fact, the present invention is not even limited to systems that track pharmaceuticals, but is also well-suited to systems that track other types of product.

In short, the present invention is limited solely by the claims that now follow.

What is claimed is:

1. A computer system for tracking the lot numbers designating particular batches of pharmaceuticals that are administered to patients comprising:
    (a) A plurality of remote systems, each comprising
        (1) one or more remote stations, each for associating the lot numbers designating particular batches of pharmaceuticals administered to patients with information relating to the patients that receive the pharmaceuticals;
        (2) a remote communication system for sending the associations to a host system;
    (b) a host system comprising:
        (1) a host communication system for receiving the associations from each of said remote systems;
        (2) a host storage area for storing the associations received by said host communication system;
        (3) a host station for receiving the lot numbers of pharmaceuticals that need to be tracked back to the patient-related information;
        (4) a host look-up system for looking up the associations related to the lot numbers that need to be tracked back to the patient-related information stored in said host storage area; and
        (5) a host notification system for issuing and delivering notice related to the lot numbers of the pharmaceuticals that need to be tracked to patients based on the associations looked-up by said host look-up system; and
    (c) a network communication system connected to each of said remote communication systems and to said host communication system for communicating the associations from each of said remote communication systems to said host communications system.

2. The system of claim 1 wherein the pharmaceuticals include blood derivatives.

3. The system of claim 1 wherein said network communication system includes the Internet.

4. The system of claim 1 wherein said network communication system includes a private dial-up network.

5. The system of claim 1 wherein at least a portion of the patient-related information is encrypted.

6. The system of claim 1 wherein at least one remote communication system initiates communication with said host communication system.

7. The system of claim 6 further including a remote storage area in said at least one remote communication system for storing the associations made by said remote station and wherein the communication is initiated periodically.

8. The system of claim 1 further including a remote storage area in at least one remote communication system for storing the associations made by said remote station and wherein said host communication system polls said at least one of said remote communication systems.

9. The system of claim 8 wherein the polling is done periodically.

10. The system of claim 1 wherein the notice is delivered to one of said remote systems over said network communication system.

11. A remote system and a host system that forms a part of a computer system for tracking the lot numbers designating particular batches of pharmaceuticals that are administered to patients, said systems comprising:
    (a) one or more remote stations, each for associating the lot numbers designating particular batches of pharmaceuticals administered to patients with information relating to the patients that receive the pharmaceuticals;
    (b) a remote communication system for sending and delivering the associations related to the lot numbers to a host system; and
    (c) a host look-up system for looking up the associations related to the lot numbers that need to be tracked back to the information relating to the patients.

12. The system of claim 11 wherein said remote system is a hospital.

13. The system of claim 11 wherein at least portions of the patient-related information are derived from one or more databases.

14. The system of claim 13 wherein the patient related information that is derived from the databases is stored in said remote storage area in one or more system fields and is contained in the databases in one or more database fields, and wherein the system further includes a map that maps each system field to its corresponding database field.

15. The system of claim 11 wherein some of the administered pharmaceuticals are marked for tracking and some are not marked for tracking and wherein at least one of said remote stations includes a data-entry software application into which information relating to the pharmaceuticals is entered and a data-monitoring software application that monitors the entry of at least portions of the information into said data-entry software application and tracks the entry of a pharmaceutical that has been marked to be tracked and does not track the entry of a pharmaceutical that has not been marked to be tracked.

16. The system of claim 15 wherein portions of the patient-related information is extracted from other databases after detection by said data-monitoring program of a pharmaceutical that is to be tracked.

17. The system of claim 11 wherein at least one of said remote systems include a first and second remote station and wherein the first remote station is positioned for use by a pharmacist and configured to allow the pharmacist to approve a requested prescription and deliver that approval to the second remote station, and wherein the second remote station is positioned for use by a technician and is configured to allow the technician to enter the lot number of the pharmaceutical that is administered to a patient pursuant to the received prescription.

18. The system of claim 17 wherein certain administered lot numbers are tracked and certain administered lot numbers are not tracked further including a printer for printing a label for the delivered prescriptions and for printing a notice only when the lot number of the pharmaceutical that is prescribed must be entered into the second remote station.

19. The system of claim 18 wherein the notice is printed on the label.

20. The system of claim 18 wherein the notice is not printed on the label.

21. The system of claim 11 wherein the patient information includes information about the diagnosis of the patient's problem for which the pharmaceutical has been prescribed.

22. The system of claim 11 wherein the patient-related information includes information indicative of an outcome following the administration of the pharmaceuticals and wherein the system further includes a remote outcome station configured to allow the entry into the system of the outcome information.

23. The system of claim 22 wherein the outcome information includes information about the effect of the administered pharmaceutical on the patient.

24. The system of claim 11 wherein the patient-related information is broken down into a plurality of categories.

25. The system of claim 24 wherein the categories include a category containing demographic information about the patient, a category containing information about the doctor who is treating the patient, and a category containing information about the pharmaceutical.

26. The system of claim 11 further including a validation system that validates whether a lot number that is entered is a valid lot number by comparing the entered lot number against a database of valid lot numbers.

27. The system of claim 26 wherein the lot number is not selected from a list of lot numbers.

28. The system of claim 11 further including a transaction tracking system for storing a historical record of operations of the system.

29. A host system that forms a part of a computer system for tracking the lot numbers designating particular batches of pharmaceuticals that are administered to patients, said host system comprising:
  (a) a host communication system for receiving from a plurality of remote systems associations of lot numbers designating particular batches of pharmaceuticals to information relating to the patients that receive the pharmaceuticals;
  (b) a host storage area for storing the associations received by said host communication system;
  (c) a host station for receiving the lot numbers of pharmaceuticals that need to be tracked back to the patient-related information;
  (d) a host look-up system for looking up the associations related to the lot numbers that need to be tracked back to the patient-related information stored in said host storage area; and
  (e) a host notification system for issuing and delivering notice of the pharmaceuticals that need to be tracked to patients based on the associations related to the lot numbers looked-up by said host look-up system.

30. The system of claim 29 containing a table listing each recipient to whom a notification should be sent and whether that notification has been successfully sent.

31. The system of claim 29 further including a warning system that issues a list of all recipients to whom a notice was not able to have been successfully sent.

32. The system of claim 29 wherein said host system further includes a validation system that validates the validity of at least portions of the patient-related information that is stored in said host storage area.

33. The system of claim 29 wherein said validation system checks with one or more other databases to obtain at least portions of the information needed to validate the validity of the patient-related information.

34. The system of claim 29 further including a validation system that validates whether a lot number that is entered is a valid lot number by comparing the entered lot number against a database of valid lot numbers.

35. The system of claim 29 further including a transaction tracking system for storing a historical record of operations of the system.

36. A method of tracking the lot numbers designating particular batches of pharmaceuticals that are administered to patients in a computer system containing a plurality of remote systems and a host system comprising:
  (a) at each remote system:
    (1) associating the lot numbers designating particular batches of pharmaceuticals administered to patients with information relating to the patients that receive the pharmaceuticals;
    (2) sending the associations to the host system;
  (b) at the host system:
    (1) receiving the associations from the remote systems;
    (2) storing the associations received from the remote systems;
    (3) receiving the lot numbers of pharmaceuticals that need to be tracked back to the patient-related information;
    (4) looking up the associations related to the lot numbers that need to be tracked back to the stored patient-related information; and
    (5) issuing and delivering notice of the pharmaceuticals that need to be tracked to patients based on the associations related to the lot numbers looked-up by said host look-up system.

37. Computer-storage media containing one or more computer programs that contain instructions to cause the following to occur in a computer system containing a plurality of remote systems and a host system:
  (a) at each remote system:
    (1) associating the lot numbers designating particular batches of pharmaceuticals administered to patients with information relating to the patients that receive the pharmaceuticals;
    (2) sending and delivering the associations related to the lot numbers to a host system; and
  (b) at the host system:
    (1) looking up the associations related to the lot numbers that need to be tracked back to the information relating to the patients.

38. Computer-storage media containing one or more computer programs that contain instructions to cause the following to occur in a computer system containing a plurality of remote systems and a host system:
  (a) at each remote system:
    (1) associating the lot numbers designating particular batches of pharmaceuticals administered to patients with information relating to the patients that receive the pharmaceuticals; and
    (2) sending the associations to the host system
  (b) at the host system:
    (1) receiving the associations from the remote systems;
    (2) storing the associations received from the remote systems;
    (3) receiving the lot numbers of pharmaceuticals that need to be tracked back to the patient-related information;
    (4) looking up the associations related to the lot numbers that need to be tracked back to the stored patient-related information; and
    (5) issuing and delivering notice of the pharmaceuticals that need to be tracked to patients based on the associations related to the lot numbers looked-up by said host look-up system.

* * * * *